United States Patent [19]

Weis

[11] 4,259,495
[45] Mar. 31, 1981

[54] PROCESS FOR PRODUCING 2,3,5,6-TETRACHLOROPYRIDINE

[75] Inventor: Claus D. Weis, Pfeffingen, Switzerland

[73] Assignee: Ciba-Geigy Corporation, Ardsley, N.Y.

[21] Appl. No.: 74,217

[22] Filed: Sep. 10, 1979

[51] Int. Cl.³ .......................................... C07D 211/68
[52] U.S. Cl. ................................................. 546/345
[58] Field of Search ........................................ 546/345

[56] References Cited

U.S. PATENT DOCUMENTS

| 3,993,654 | 11/1976 | Dean et al. | 546/345 |
| 4,111,938 | 9/1978 | Redemann | 546/345 |

FOREIGN PATENT DOCUMENTS 539034 12/1976 U.S.S.R. ................................... 546/345

*Primary Examiner*—Ethel G. Love
*Attorney, Agent, or Firm*—Karl F. Jorda

[57] ABSTRACT

A novel process for producing 2,3,5,6-tetrachloropyridine is described. In this process, pentachloropyridine is reacted, in an alkanephosphonic acid dialkyl ester (dialkyl alkane phosphonate) having 1 to 4 carbon atoms in each of the alkyl groups or in a phosphoric acid trialkyl ester (trialkyl phosphate) having 1 to 4 carbon atoms in each of the alkyl groups as the solvent, at 60° to 120° C., in the presence of 1.4 to 2.8 mols, per mol of pentachloropyridine, of an ammonium salt of an inorganic or organic acid, with 1.2 to 1.6 gram atoms of zinc per mol of pentachloropyridine, with selective dechlorination of the pentachloropyridine in the 4-position occurring.

2,3,5,6-Tetrachloropyridine is a valuable commercial product, which can be used for producing insecticidal formulations. Furthermore, 2,3,5,6-tetrachloropyridine is used as intermediate for the production of herbicidally effective α-[4-(3',5',6'-trichloropyrid-2'-yloxy)-phenoxy]-alkanecarboxylic acids and derivatives thereof.

There are also described novel ammonium salts of methanephosphonic acid monomethyl ester, in the presence of which the selective dechlorination of pentachloropyridine in the 4-position can be advantageously performed.

9 Claims, No Drawings

PROCESS FOR PRODUCING 2,3,5,6-TETRACHLOROPYRIDINE

The present invention relates to a process for producing 2,3,5,6-tetrachloropyridine from pentachloropyridine.

2,3,5,6-Tetrachloropyridine is a valuable commercial product which can be used for the production of insecticidal formulations. Furthermore, 2,3,5,6-tetrachloropyridine is used as an intermediate for producing herbicidally effective α-[4-(3′,5′,6′-trichloropyrid-2′-yloxy)-phenoxy]-alkanecarboxylic acids and derivatives thereof. The production and use of such α-[4-(3′,5′,6′-trichloropyrid-2′-yloxy)-phenoxy]-alkanecarboxylic acids and derivatives thereof are described for example in the U.S. Pat. No. 4,133,675.

The method of producing 2,3,5,6-tetrachloropyridine by reaction of pentachloropyridine with zinc and hydrochloric acid in an alcoholic or aqueous reaction medium is known. In an aqueous reaction medium, the reaction is performed at temperatures of 110° to 160° C. under the pressure corresponding to the applied reaction temperature. There are obtained conversions of pentachloropyridine of 82.5% to 96.9% and yields of 87.6% to 94.6% (see U.S. Pat. No. 3,993,654). Dichloropyridines and trichloropyridines occur as by-products. The formation of these by-products increases with increasing conversion of pentachloropyridine.

2,3,5,6-Tetrachloropyridine can indeed be produced in good yield by this known process, but the process has the disadvantage that it has to be carried out under pressure and hence requires a considerable expenditure on apparatus.

It is therefore the object of the present invention to provide a process by which 2,3,5,6-tetrachloropyridine can be produced in good yields in a simple manner under normal pressure.

According to the present invention, 2,3,5,6-tetrachloropyridine is produced by reacting pentachloropyridine, in an alkanephosphonic acid dialkyl ester (dialkyl alkane phosphonate) having 1 to 4 carbon atoms in each of the alkyl groups or in a phosphoric acid trialkyl ester (trialkyl phosphate) having 1 to 4 carbon atoms in each of the alkyl groups as the solvent, at 60° to 120° C., in the presence of 1.4 to 2.8 mols, per mol of pentachloropyridine, of an ammonium salt of an inorganic or organic acid, with 1.2 to 1.6 gram atoms of zinc per mol of pentachloropyridine.

Suitable alkanephosphonic acid dialkyl esters which can be used according to the invention as solvents are for example: the dimethyl, diethyl, di-n-propyl, diisopropyl, di-n-butyl, di-sec-butyl, diisobutyl and di-tert-butyl esters of methane-, ethane-, 1-methylethane-, 1,1-dimethylethane-, propane-, 1-methylpropane-, 2-methylpropane- and butanephosphonic acid. Preferred alkanephosphonic acid dialkyl esters are methanephosphonic acid dimethyl ester and ethanephosphonic acid diethyl ester.

Suitable phosphoric acid trialkyl esters which can be used according to the invention as solvents are for example: phosphoric acid trimethyl ester, phosphoric acid triethyl ester, phosphoric acid tri-n-propyl ester, phosphoric acid triisopropyl ester and phosphoric acid tributyl ester. Preferred phosphoric acid trialkyl esters are phosphoric acid trimethyl ester and phosphoric acid triethyl ester.

Within the temperature range of 60° to 120° C., in which the process according to the invention can be performed, temperatures of 85° to 90° C. are preferred.

The ammonium salts usable according to the invention contain as cation the ammonium ion, or the derivatives derived therefrom by partial or complete replacement of the hydrogen atoms by alkyl and/or phenyl groups, whereby the phenyl groups can be substituted by simple substituents such as alkyl, alkoxy or halogen. The ammonium salts usable according to the invention contain as anion the radical of any inorganic or organic acid capable of forming ammonium salts.

Advantageously applicable ammonium salts correspond to the formula

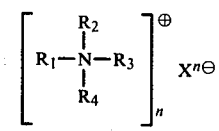

in which $R_1$, $R_2$, $R_3$ and $R_4$ can be identical or different and are each hydrogen, alkyl having 1 to 4 carbon atoms, or phenyl which can be substituted by halogen, by alkyl groups having 1 to 4 carbon atoms or by alkoxy groups having 1 to 4 carbon atoms, X is an anion from the group: chloride, bromide, sulfate, hydrogen sulfate, phosphate, hydrogen phosphate, dihydrogen phosphate, carbonate, hydrogen carbonate, acetate, propionate, butyrate, isobutyrate, oxalate, benzoate, alkanephosphonate having 1 to 4 carbon atoms in the alkyl group and alkane- or benzenesulfonate having 1 to 4 carbon atoms in the alkyl group, and n is 1 to 3 and corresponds to the number of negative charges of the respective anion X.

To be mentioned as further ammonium salts that can be advantageously used are the ammonium salts of methanephosphonic acid monomethyl ester of the formula

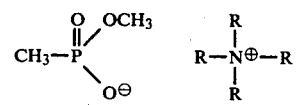

in which R is hydrogen or methyl. These ammonium salts are novel compounds which can be obtained, in a simple manner, by heating ammonium chloride or tetramethyl-ammonium chloride in methanephosphonic acid dimethyl ester to 150° C., with methyl chloride being split off. The reaction is advantageously performed in excess methanephosphonic acid dimethyl ester as solvent. After completion of the reaction, the excess methanephosphonic acid dimethyl ester is distilled off in vacuo, and the ammonium salt, optionally after digestion in a suitable solvent, for example acetone, methyl ethyl ketone or ether, is obtained in crystalline form.

Preferred ammonium salts are ammonium chloride, ammonium sulfate, ammonium carbonate, the ammonium salt of methanephosphonic acid monomethyl ester and the tetramethylammonium salt of methanephosphonic acid monomethyl ester.

With the use of methanephosphonic acid dialkyl ester as solvent, the aforementioned ammonium salts are used preferably in an amount of 1.6 mols per mol of pentachloropyridine. With the use of ethanephosphonic acid dialkyl ester or trialkylphosphate as solvent, there are preferably used 2.6 to 2.8 mols of ammonium salt per mol of pentachloropyridine.

The zinc to be used according to the invention is used in the form of zinc chips or preferably in the form of zinc dust. There are preferably used 1.2–1.3 gram atoms of zinc per mol of pentachloropyridine.

It is possible by the process according to the invention to perform the selective dichlorination of pentachloropyridine to 2,3,5,6-tetrachloropyridine at normal pressure. 2,3,5,6-Tetrachloropyridine is obtained by this process in a yield of about 92% of theory, and in a degree of purity of 97%.

The process according to the invention is further illustrated by the following Examples.

EXAMPLE 1

12.76 g (0.05 mol) of pentachloropyridine is dissolved, by heating at 90° C., in 80 ml of dimethylmethanephosphonate. After the addition of 4.1 g (0.063 gram atom) of zinc dust, there is added dropwise to the clear solution in the course of 20 minutes, with vigorous stirring, a solution of 4.26 g (0.08 mol) of ammonium chloride in 15 ml of water. After the addition of the ammonium chloride solution has been completed, stirring is continued for 40 minutes. The reaction mixture obtained is then filtered hot, and the filter residue is washed with 10 ml of dimethylmethanephosphonate. The filtrate is poured into 500 ml of ice water; there is then added 12.5 ml of concentrated hydrochloric acid and the mixture is stirred for 2 hours. The 2,3,5,6-tetrachloropyridine, which has precipitated in the form of white crystals, is subsequently washed with 150 ml of water and dried. In this manner is obtained 10.0 g (90.8% of theory) of 2,3,5,6-tetrachloropyridine having a melting point of 89° to 90° C. According to gas-chromatographical analysis, the product contains 97.0% of 2,3,5,6-tetrachloropyridine, 0.5% of 2,3,5-trichloropyridine, 0.6% of 2,3,6-trichloropyridine and 1.6% of pentachloropyridine.

EXAMPLE 2

1.84 g (0.0281 gram atom) of zinc dust is introduced into a solution, heated to 80° C., of 5.1 g (0.02 mol) of pentachloropyridine in 35 ml of dimethylmethanephosphonate. A solution of 2.44 g (0.0254 mol) of ammonium carbonate in 10 ml of water is subsequently added dropwise at a temperature of 90° to 95° C. in the course of 70 minutes with vigorous stirring. The reaction mixture is then stirred into 250 ml of ice water; there is added 5 ml of concentrated hydrochloric acid and the mixture is stirred for a further 10 minutes, and is subsequently extracted twice with 100 ml of ether each time. The combined extracts are washed with 70 ml of water, dried over sodium sulfate, filtered, and evaporated to dryness to yield as residue 4.05 g (92% of theory) of 2,3,5,6-tetrachloropyridine having a melting point of 86° to 88° C. According to gas-chromatographical analysis, the product contains 93.4% of 2,3,5,6-tetrachloropyridine, 2.1% of 2,3,5-trichloropyridine, 2.2% of 2,3,6-trichloropyridine and 0.8% of pentachloropyridine.

EXAMPLE 3

On reaction of 12.76 g (0.05 mol) of pentachloropyridine with 4.1 g (0.063 gram atom) of zinc dust and 11.6 g (0.08 mol) of ammonium sulfate using the method described in Example 1, there is obtained 10.1 g (92% of theory) of crude 2,3,5,6-tetrachloropyridine, which contains, according to gas-chromatographical analysis, 92% of 2,3,5,6-tetrachloropyridine, 3.3% of 2,3,5-trichloropyridine, 1.3% of 2,3,6-trichloropyridine and 2.9% of pentachloropyridine.

EXAMPLE 4

On reaction of 12.76 g (0.05 mol) of pentachloropyridine with 4.1 g (0.063 gram atom) of zinc dust and 10.6 g (0.08 mol) of diammonium hydrogen phosphate using the method described in Example 1, there is obtained 10.2 g (93% of theory) of crude 2,3,5,6-tetrachloropyridine, which contains, according to gas-chromatographical analysis, 95.1% of 2,3,5,6-tetrachloropyridine, 0.8% of 2,3,5-trichloropyridine, 0.5% of 2,3,6-trichloropyridine and 3.6% of pentachloropyridine.

EXAMPLE 5

4.6 g (0.07 gram atom) of zinc dust is introduced into a solution, heated to 90° C., of 12.57 g (0.05 mol) of pentachloropyridine in 150 ml of dimethylmethanephosphonate, and there is then added dropwise in the course of 25 minutes, with stirring, a solution of 9.52 g (0.075 mol) of the ammonium salt of methanephosphonic acid monomethyl ester in 44 ml of water. After the addition of the ammonium salt has been completed, the reaction mixture is firstly stirred for 30 minutes, subsequently filtered hot, and the filter residue is washed with 10 ml of dimethylmethanephosphonate. The filtrate is poured into 500 ml of ice water; 12.5 ml of concentrated hydrochloric acid is then added and the mixture is stirred for 2 hours. The crystals which have precipitated are afterwards filtered off, washed with 150 ml of water and dried to yield 8.72 g (80.4% of theory) of crude 2,3,5,6-tetrachloropyridine, m.p. 88° to 89° C., which contains, according to gas-chromatographical analysis, 94.1% of 2,3,5,6-tetrachloropyridine, 2.5% of 2,3,5-trichloropyridine, 1.9% of 2,3,6-trichloropyridine and 0.17% of pentachloropyridine.

The ammonium salt of the methanephosphonic acid monomethyl ester can be produced as follows:

In a 1-liter round-bottomed flask with mounted reflux condenser, 540 g (4mols) of dimethylmethanephosphonate and 107 g (2 mols) of ammonium chloride are heated with stirring to 110° C., with the reaction commencing with the evolution of methyl chloride. The temperature is then raised within 20 minutes to 138° C., and subsequently within a further 20 minutes to 151° C. The clear colourless solution is afterwards evaporated to dryness at 12 Torr to obtain as residue a yellow oil which, after the addition of 500 ml of acetone, is stirred for 24 hours, in the course of which crystallisation occurs. The crystal suspension is cooled to 0° C., filtered, and then washed on the filter, with the exclusion of moisture, with 150 ml of ether. After drying at 50° C. under 12 Torr, there is obtained 118.6 g (46.7% of theory) of the ammonium salt of methanephosphonic acid monoethyl ester, m.p. 96° to 103° C., in the form of highly hydroscopic crystals, which soon deliquesce on standing in air.

EXAMPLE 6

A suspension of 12.8 g (0.05 mol) of pentachloropyridine and 4.1 g (0.062 gram atom) of zinc dust in 120 ml of dimethylmethanephosphonate is heated with stirring to 80° C. There is then added dropwise within 15 minutes a solution of 13.76 g (0.075 mol) of the tetramethylammonium salt of methanephosphonic acid monomethyl ester in 30 ml of water. The mixture is subsequently filtered hot, the filter residue is washed with 30 ml of dimethylmethanephosphonate, and the filtrate is poured into 600 ml of ice water containing 12.5 ml of concentrated hydrochloric acid. The resulting white crystal suspension is stirred for 30 minutes; it is then filtered, and the filter residue is washed with water and dried to yield 9.95 g (90% of theory) of crude 2,3,5,6-tetrachloropyridine, m.p. 87.5° to 89° C., which contains, according to gas-chromatographical analysis, 96.9% of 2,3,5,6-tetrachloropyridine, 1.6% of 2,3,5-trichloropyridine, 0.9% of 2,3,6-trichloropyridine and 0.6% of pentachloropyridine.

The employed tetramethylammonium salt of methanephosphonic acid monomethyl ester can be produced as follows:

In a 1-liter flask with mounted reflux condenser, 540 g (4 mols) of dimethylmethanephosphonate and 219 g (2 mols) of tetramethylammonium chloride are heated, with stirring, to 130° C., in the course of which the reaction commences with the evolution of methyl choride. The temperature is then raised within 3 hours to 150° C., and the reaction mixture is afterwards heated at 160° C. for a further one hour. The clear colourless solution is evaporated under 12 Torr to dryness, and 400 ml of acetone is added to the white crystalline residue; the mixture is subsequently stirred for 30 minutes at 0° C. and then filtered. The residue is washed with 500 ml of ether, and dried at 60° C. and 12 Torr over solid potassium hydroxide to thus obtain 312 g (85% of theory) of tetramethylammonium salt of methanephosphonic acid monomethyl ester, m.p. 172° to 177° C. (decomposition), in the form of white crystals.

EXAMPLE 7

A suspension of 8.22 g (0.075 mol) of tetramethylammonium chloride in 90 ml of dimethylmethanephosphonate is heated for 1 hour at 160° C. It is then cooled to 90° C., and 12.57 g (0.05 mol) of pentachloropyridine and 3 ml of water are added. There is subsequently added portionwise, in the course of 30 minutes, 4.1 g (0.063 gram atom) of zinc dust. After completion of the addition of the zinc dust, the mixture is firstly stirred for 20 minutes and then filtered. The filtrate is poured into a solution of 12.5 ml of concentrated hydrochloric acid in 500 ml of water, and stirring is maintained for 2 hours. After filtration, the filter residue is washed with water and dried to yield 9.1 g (83.9% of theory) of crude 2,3,5,6-tetrachloropyridine which has a melting point of 88° to 89° C. and which contains, according to gas-chromatographical analysis, 91.25% of 2,3,5,6-tetrachloropyridine, 2.66% of 2,3,5-trichloropyridine, 2.59% of 2,3,6-trichloropyridine and 0.5% of pentachloropyridine.

EXAMPLE 8

Using the method described in Example 1, 12.76 g (0.05 mol) of pentachloropyridine is reacted with 4.1 g (0.063 gram atom) of zinc dust and 7.22 g (0.135 mol) of ammonium chloride, the solvent being in this case diethylethanephosphonate instead of dimethylmethanephosphonate. There is obtained 10.2 g (93% of theory) of crude 2,3,5,6-tetrachloropyridine, m.p. 86° to 88° C., which contains, according to gas-chromatographical analysis, 92.7% of 2,3,5,6-tetrachloropyridine, 1.2% of 2,3,5-trichloropyridine, 2.2% of 2,3,6-trichloropyridine and 2.8% of pentachloropyridine.

EXAMPLE 9

Using the method described in Example 2, 12.76 g (0.05 mol) of pentachloropyridine is reacted with 4.1 g. (0.063 gram atom) of zinc dust and 13.21 g (0.138 mol) of ammonium carbonate, the solvent used being however diethylethanephosphonate in place of dimethylmethanephosphonate. The yield is 10.3 g (93.5% of theory) of 2,3,5,6-tetrachloropyridine having a melting point of 86° to 88° C.

EXAMPLE 10

1.7 g (0.027 gram atom) of zinc dust is introduced into a solution, heated to 80° C., of 5.1 g (0.02 mol) of pentachloropyridine in 35 ml of trimethylphosphate, and there is subsequently added dropwise within 1 hour at 80° to 83° C., with vigorous stirring, a solution of 2.84 g (0.055 mol) of ammonium chloride in 10 ml of water. The reaction mixture is then poured into 250 ml of ice water; 5 ml of concentrated hydrochloric acid is added and stirring is continued for 10 minutes. The mixture obtained is afterwards extracted twice with 100 ml of ether each time; the combined ether extracts are washed with 70 ml of water and dried over sodium sulfate. The ether is evaporated off to leave 4.1 g (93.2% of theory) of crude 2,3,5,6-tetrachloropyridine, m.p. 86° to 88° C., which contains, according to gas-chromatographical analysis, 94.1% of 2,3,5,6-tetrachloropyridine, 2.0% of 2,3,5-trichloropyridine, 2.0% of 2,3,6-trichloropyridine and 2.8% of pentachloropyridine.

EXAMPLE 11

Using the method described in Example 10, 5.1 g (0.02 mol) of pentachloropyridine is reacted with 1.7 g (0.027 gram atom) of zinc dust and 5.3 g (0.055 mol) of ammonium carbonate. The yield is 4.1 g (93.2% of theory) of 2,3,5,6-tetrachloropyridine having a melting point of 86° to 88° C.

EXAMPLE 12

Using the method described in Example 10, 5.1 g (0.02 mol) of pentachloropyridine is reacted with 1.7 g (0.027 gram atom) of zinc dust and 2.84 g (0.055 mol) of ammonium chloride, the solvent used however being triethyl phosphate instead of trimethyl phosphate. The yield obtained is 4.05 g (93.1% of theory) of 2,3,5,6-tetrachloropyridine having a melting point of 86° to 88° C.

EXAMPLE 13

Using the method described in Example 11, 5.1 g (0.02 mol) of pentachloropyridine is reacted with 1.7 g (0.027 gram atom) of zinc dust and 5.3 g (0.055 mol) of ammonium carbonate, the solvent used in this case being however triethyl phosphate instead of trimethyl phosphate. The yield obtained is 4.1 g (93.2% of theory) of 2,3,5,6-tetrachloropyridine having a melting point of 86° to 88° C.

What is claimed is:

1. A process for producing 2,3,5,6-tetrachloropyridine by dechlorination of pentachloropyridine, which process comprises reacting pentachloropyridine, in an alkanephosphonic acid dialkyl ester having 1 to 4 carbon atoms in each of the alkyl groups or in a phosphoric acid trialkyl ester having 1 to 4 carbon atoms in each of the alkyl groups as the solvent, at 60° to 120° C., in the presence of 1.4 to 2.8 mols, per mol of pentachloropyridine, of an ammonium salt of an inorganic or organic acid, with 1.2 to 1.6 gram atoms of zinc per mol of pentrachoropyridine, said ammonium salt having the formula

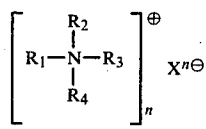

in which $R_1$, $R_2$, $R_3$ and $R_4$ can be identical or different and are each hydrogen, alkyl having 1 to 4 carbon atoms, or phenyl which can be substituted by halogen, by alkyl groups have 1 to 4 carbon atoms or by alkoxy groups having 1 to 4 carbon atoms, X is an anion from the group: chloride, bromide, sulfate, hydrogen sulfate, phosphate, hydrogen phosphate, dihydrogen phosphate, carbonate, hydrogen carbonate, acetate, propionate, butyrate, isobutyrate, oxalate, benzoate, alkanephosphonate having 1 to 4 carbon atoms in the alkyl group and alkane- or benzene sulfonate having 1 to 4 carbon atoms in the alkyl group, and n is 1 to 3 and corresponds to the number of negative charges of the respective anion X.

2. A process according to claim 1, wherein the alkanephosphonic acid dialkyl ester used is methanephosphonic acid dimethyl ester or ethanephosphonic acid diethyl ester.

3. A process according to claim 1, wherein the phosphoric acid trialkyl ester used is phosphoric acid trimethyl ester or phosphoric acid triethyl ester.

4. A process according to claim 1, wherein the dechlorination of the pentachloropyridine is performed at 85° to 90° C.

5. A process according to claim 1, wherein there is used an ammonium salt of O-methyl-methanephosphonic acid of the formula

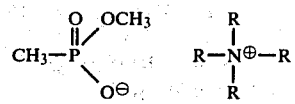

in which R is hydrogen or methyl.

6. A process according to claim 1, wherein the ammonium salt used is: ammonium chloride, ammonium sulfate, ammonium carbonate, the ammonium salt of methanephosphonic acid monomethyl ester or the tetramethylammonium salt of methanephosphonic acid monomethyl ester.

7. A process according to claim 1, wherein, with the use of methanephosphonic acid dialkyl ester as solvent, there are used 1.6 mols of ammonium salt per mol of pentachloropyridine.

8. A process according to claim 1, wherein, with the use of ethanephosphonic acid dialkyl ester or trialkyl phosphate as solvent, there are used 2.6 to 2.8 mols of ammonium salt per mol of pentachloropyridine.

9. A process according to claim 1, wherein 1.20 to 1.30 gram atoms of zinc are used per mol of pentachloropyridine.

* * * * *

UNITED STATES PATENT AND TRADEMARK OFFICE
CERTIFICATE OF CORRECTION

PATENT NO. : 4,259,495
DATED : MARCH 31, 1981
INVENTOR(S) : CLAUS D. WEIS AND PETER SUTTER

It is certified that error appears in the above—identified patent and that said Letters Patent is hereby corrected as shown below:

COVER PAGE, SECTION NO. 75, INVENTOR READS:

"Claus D. Weis, Pfeffingen, Switzerland"

should read:

"Claus D. Weis, Pfeffingen, Switzerland and Peter Sutter, Muttenz, Switzerland".

Signed and Sealed this

Thirtieth Day of June 1981

[SEAL]

Attest:

RENE D. TEGTMEYER

Attesting Officer     Acting Commissioner of Patents and Trademarks